(12) United States Patent
Beilfuss et al.

(10) Patent No.: US 6,469,060 B2
(45) Date of Patent: *Oct. 22, 2002

(54) COMPOSITIONS BASED ON IODOPROPYNYL-AND FORMALDEHYDE DONOR COMPOUNDS AND TO THEIR USE AS PRESERVATIVES

(75) Inventors: Wolfgang Beilfuss, Hamburg (DE); Wolfgang Siegert, Ellerau (DE); Klaus Weber, Hamburg (DE)

(73) Assignee: Air Liquide Sante (International), Paris (FR)

( * ) Notice: Subject to any disclaimer, the term of this patent is extended or adjusted under 35 U.S.C. 154(b) by 148 days.

This patent is subject to a terminal disclaimer.

(21) Appl. No.: 09/861,586

(22) Filed: May 22, 2001

(65) Prior Publication Data

US 2001/0034366 A1 Oct. 25, 2001

Related U.S. Application Data

(62) Division of application No. 09/424,447, filed as application No. PCT/IB98/00766 on May 19, 1998, now Pat. No. 6,355,679.

(30) Foreign Application Priority Data

May 23, 1997  (DE) .......................... 197 22 858

(51) Int. Cl.⁷ ................ A01N 43/26; A01N 31/14; A01N 37/00; A01N 43/76
(52) U.S. Cl. ............... 514/529; 514/228.8; 514/374; 514/463; 514/722
(58) Field of Search ............... 514/529, 228.8, 514/374, 463, 722

(56) References Cited

U.S. PATENT DOCUMENTS

| | | | |
|---|---|---|---|
| 4,040,977 A | | 8/1977 | Eggensperger et al. |
| 4,166,122 A | * | 8/1979 | Paulus et al. ............... 523/122 |
| 5,246,913 A | | 9/1993 | Hsu |
| 5,332,765 A | * | 7/1994 | Lorentzen et al. .......... 523/122 |
| 5,464,622 A | | 11/1995 | Mehta et al. |

FOREIGN PATENT DOCUMENTS

| | | | |
|---|---|---|---|
| CN | 1127772 | * | 7/1996 |
| DE | 2711106 | | 9/1978 |
| EP | 0327220 | | 8/1989 |
| EP | 0484172 | | 5/1992 |
| EP | 0547480 | | 6/1993 |
| EP | 0668014 | | 8/1995 |
| JP | 60217233 | * | 10/1985 |
| JP | 6145014 | | 5/1995 |
| WO | WO 9529588 | | 11/1995 |
| WO | WO 9638043 | | 12/1996 |

OTHER PUBLICATIONS

W. Anker, "Preservation of Water–Based Cooling Lubricating Oils", *Microb. Materializerstoerung Materialschutz* (1995), pp. 151–161.

K.H. Schuelke et al., "Coolant Preservatives", *Tribologie+ Schmierungstechnik* (1985), pp. 220–225.

* cited by examiner

*Primary Examiner*—Alton Pryor
(74) *Attorney, Agent, or Firm*—Young & Thompson

(57) ABSTRACT

Compositions having broad effectiveness against bacterial and fungi, which comprise (a) an iodopropynylbutyl compound and (b) one or more formaldehyde donor compounds, the formaldehyde donor compounds being N-formals, O-formals and/or a combination thereof. The compositions are also stable and effective in the form of liquid concentrates. The present invention also relates to the use of such compositions in industrial products and to industrial products which comprise these compositions.

24 Claims, No Drawings

COMPOSITIONS BASED ON IODOPROPYNYL-AND FORMALDEHYDE DONOR COMPOUNDS AND TO THEIR USE AS PRESERVATIVES

CROSS REFERENCE TO RELATED APPLICATION

This application is a divisional application of application Ser. No. 09/424,447 filed on Nov. 23, 1999 now U.S. Pat. No. 6,355,679, which is the 35 USC 371 national stage of International Application PCT/IB98/00766 filed on May 19, 1998.

FIELD OF THE INVENTION

The present invention relates to compositions or preservatives for use in industrial products, which protect these products against bacterial and fungal infestation over extended service lives.

BACKGROUND OF THE INVENTION

Preservatives having a biocidal action for use in industrial products such as cutting fluids, cutting fluids which have been mixed with water, industrial emulsions or other water-based industrial products, and also for household products, such as, for example, cleaning products or cosmetics, such as, for example, bodycare products, are when required generally added to the products to be preserved in low concentration in the form of concentrates.

They protect these products against infestation by bacteria, fungi and yeasts and contribute to long service lives of industrial products, such as, for example, cutting fluids which have been mixed with water, and to a long useful life of household products and cosmetic products.

During their manufacture, storage and their use, preservatives are subject to certain requirements which arise inter alia from the way in which they are added to the above-mentioned products in the form of liquid concentrates.

A known fungicidal active ingredient which is frequently used today is iodopropynylbutyl carbamate (IPBC), which is marketed, for example, by Troy Chemie as an organic fungicide preparation in the form of a 20% strength solution of the active ingredient in glycols under the trade name Troyshield F20.

In order to achieve a likewise satisfactory bactericidal effect, it is, however, necessary to combine IPBC with other active substances, e.g. formaldehyde donor compounds. Regarding compatibility with IPBC, however, there are problems when used in concentrates containing formaldehyde donor compounds in the form of strongly alkaline bactericides. Thus, for example, Troy Chemie's technical instruction sheet for Troyshield F20™ advises against mixing it with strongly alkaline bactericides, such as, for example, 1,3,5-tris(hydroxyethyl)hexahydrotriazine (Grotan BK™), because the stability of fungicidally and bactericidally active preparations based on IPBC is impaired.

There has thus been a search for potential ways of improving the stability of IPBC-based compositions for use as preservatives having a fungicidal and bactericidal action.

The prior art includes, for example, an almost white powder consisting of IPBC and a mixture of 1,3-bis(hydroxymethyl)-5,5-dimethylhydantoin and hydroxymethyl-5,5-dimethylhydantoin GlydantPlus™, Lonza AG), which is used as a preservative for cosmetic preparations.

U.S. Pat. No. 5,496,842 and U.S. Pat. No. 5,428,050 disclose water-soluble compositions comprising a combination of iodopropynylbutyl compounds and N-methylol compounds. It is disclosed that compositions comprising IPBC and N-methylol compounds in a weight ratio of from 1:100 to 1:2000 are in the form of a concentrate powder which, as a water-soluble additive, can be added to industrial products, in particular bodycare products, which then include from 0.01% to 2% of these compositions. The N-methylol compounds mentioned in U.S. Pat. No. 5,496,842 and U.S. Pat. No. 5,428,050 do, however, include compounds which are not compatible with IPBC, for example 1,3,5-tris(hydroxyethyl)-hexahydrotriazine.

EP 0327220 B1 discloses a combination of an iodopropynyl compound with known formaldehyde donors. The disclosed compositions include, as preferred iodopropynyl compound, IPBC and, as formaldehyde donors, non-toxic and odorless compounds which are suitable for use in bodycare products, for example urea derivatives and dimethyloldimethylhydantoin. The compositions of EP 0327200 B1 are likewise added, for example, in the form of solid, water-soluble mixtures, to the products to be preserved.

The known pulverulent concentrates do, however, have a number of technical disadvantages, such as, for example, a tendency toward clumping, a relatively low dissolution rate, a tendency to form dust and the like.

Moreover, the use of odourless, i.e. usually nonvolatile, formaldehyde donors does not, in the case of certain applications, offer adequate antimicrobial protection in the gaseous phase, since no vapour phase of volatile, formaldehyde compounds is present.

In addition, the N-methylols in the form of liquid concentrates mentioned in U.S. Pat. No. 5,496,842 and U.S. Pat. No. 5,428,050 are not compatible with IPBC, i.e. are unstable and are thus also insufficiently stable in liquid products, such as cutting fluids, which are to be preserved. This is therefore a disadvantage particularly because in industrial products such as cutting fluid emulsions, desired pH stabilization and buffering is achieved inter alia by adding basic, tertiary amines.

SUMMARY OF THE INVENTION

The object of the present invention is to provide compositions which protect industrial products against bacterial attack and fungal infestation over extended service lives. The novel compositions should themselves be sufficiently stable and should not decompose under various conditions. In addition, they should be easy to handle and have advantageous technical properties and be easily incorporated into industrial products.

Another object of the present invention is to provide biocidal compositions which include iodopropynylbutyl compounds and formaldehyde donor compounds which are compatible therewith. It should be possible to meter these compositions into standard commercial industrial products, for example by adding a liquid preparation.

Another aim of the present invention is to provide compositions which have improved vapour phase effectiveness compared with the prior art and are sufficiently stable over a wide pH range.

A further object of the present invention is to provide industrial products, such as, for example, cutting fluids, which are distinguished from the prior art by increased stability and improved effectiveness.

This object is achieved by a composition which includes (a) an iodopropynylbutyl compound selected from iodopropynylbutyl esters, ethers, acetals, carbamates and carbonates and (b) one or more formaldehyde donor compounds, and is characterized in that the formaldehyde donor compounds are N-formals formed by the reaction or condensation of a monovalent or polyvalent, amino-substituted $C_1$–$C_{10}$-alkyl, -aryl or -aralkyl alcohol and a formaldehyde-supplying compound, and/or O-formals formed by the reaction of a monovalent or polyvalent $C_1$–$C_{10}$-alkyl, -aryl -aralkyl alcohol or of a glycol or glycol ether and a formaldehyde-supplying compound, and/or a combination thereof.

DESCRIPTION OF THE PREFERRED EMBODIMENTS

The novel preparations preferably comprise iodopropynylbutyl carbamate (IPBC), and the formaldehyde donor compound is preferably an N-formal selected from 3,3'-methylenebis(5-methyloxazolidine) (Mar 71™), 3,3'-methylenebis(tetrahydro-2H-1,3-oxazine) and 1-aza-5-ethyl-3,7-dioxabicyclo-(3,3,0)octane, particularly preferably a combination of 3,3'-methylenebis(5-methyloxazolidine) (Mar 71™) and IPBC.

The compositions comprising the novel iodopropynylbutyl compound and N-formals include the components in amounts, based on the composition, of from 0.1 to 20% by weight of iodopropynylbutyl compound and from 99.9 to 80% by weight of N-formal, preferably from 1 to 10% by weight of iodopropynylbutyl compound and from 99 to 90% by weight of N-formal. The composition particularly preferably comprises from 4 to 6% by weight of iodopropynylbutyl compound, in particular iodopropynylbutyl carbamate, and from 96 to 94% by weight of N-formal, in particular 3,3'-methylenebis(5-methyloxazolidine).

In addition or alternatively to the N-formals according to the invention, the novel compositions may also comprise O-formals formed by the reaction or condensation of formaldehyde-supplying compounds and mono- or polyvalent $C_1$–$C_{10}$-alkyl, -aryl or -aralkyl alcohols or glycols or glycol ethers, such as, for example, 1,2-propylene glycol hemiformal, ethylene glycol mono- and/or bisformal, butyldiglycol hemiformal, butylglycol hemiformal, benzyl glycol hemiformal, dipropylene glycol hemiformal and the like.

The compositions comprising the iodopropynylbutyl compound according to the invention and O-formals include the components in amounts, based on the composition, of from 0.1 to 20% by weight of iodopropynylbutyl compound and from 99.9 to 80% by weight of O-formal, preferably from 1 to 10% by weight of iodopropynylbutyl compound and from 99 to 90% by weight of O-formal. The composition particularly preferably comprises from 4 to 6% by weight of iodopropynylbutyl compound, in particular iodopropynylbutyl carbamate and from 96 to 94% by weight of O-formal, in particular from 96 to 94% by weight of 1,2-propylene glycol hemiformal.

Particularly suitable compositions are also those which comprise from 0.1 to 20% by weight, of an iodopropynylbutyl compound and from 99.9 to 80% by weight of a mixture of N- and O-formals, the weight ratio of N- to O-formals being from 10:1 to 1:10, preferably from 9:1 to 8:2 and particularly preferably from 2:1 to 1:2. These compositions preferably comprise from 1 to 10% by weight of iodopropynylbutyl compound and from 99 to 90% by weight of the mixture of N- and O-formals. Such a composition particularly preferably comprises from 4 to 6% by weight of iodopropynylbutyl compound, in particular iodopropynylbutyl carbamate, and from 96 to 94% by weight of the mixture of N- and O-formals, in particular from 96 to 94% by weight of a mixture of 3,3'-methylenebis (5-methyloxazolidine) and 1,2-propylene glycol hemiformal.

The novel compositions are preferably in stable liquid, viscous liquid or paste form, so that they are easy to handle and can be added easily to an industrial product at any time in order to preserve it.

In addition to the biocidally effective components, the novel compositions may comprise further additives and/or auxiliaries, such as emission-reducing additives, viscosity-modifying additives, wetting agents and solvents which have a favourable effect on the technical properties of the compositions, such as, for example, solubility in water, in total amounts of less than 90% by weight, preferably of less than 30% by weight and particularly preferably of less than 15% by weight. Here, the mixing ratios of the individual additives to one another are in the customary ranges known for biocidal compositions.

Particularly suitable compositions are those which comprise a solvent which is selected from 1,2-propylene glycol, 1-methoxy-2-propanol, phenoxypropanol and phenoxyethanol.

For example, the addition of certain glycols, preferably 1,2-propylene glycol, in amounts of from 1 to 20% by weight, based on the composition, has a positive influence on the odor of the compositions and reduces the emission of readily volatile substances, such as, for example, formaldehyde.

Particularly suitable compositions are those which, based on the composition, include the following components:
  a) from 0.1 to 20% by weight, preferably from 1 to 10% by weight and particularly preferably from 4 to 6% by weight, of an iodopropynyl compound according to the invention and
  b) from 99.8 to 80% by weight, preferably from 99 to 90% by weight and particularly preferably from 96 to 94% by weight, of a mixture of solvents and N-formals according to the invention or of a mixture of solvents and O-formals according to the invention or of a mixture of a combination of N- and O-formals and solvents and also other additives as described above, the weight ratio of formal to a solvent being from 50:1 to 1:10 and preferably greater than 9:1.

As well as the described additives and solvents, which contribute to improving the properties of the novel compositions, the latter may comprise further known biocidal active ingredients, such as, for example, isothiazolones or mercaptopyridines, of which N-octylisothiazolone (Kathon 893™) and 2-mercaptopyridine N-oxide, in particular in the form of its 40% strength aqueous sodium salt solution (Pyrion-Na™), are particularly preferred;

The composition may also comprise further additives which improve its stability.

In a specific embodiment of the present invention, the composition, as described above? comprises between 1% and 10% by weight of IPBC, between 85% and 98,5% by weight of 3-3'-methylene bis (5-methyloxazolidine) and between 0,5% and 5% by weight of a stabilizer selected from triethanolamine, pyriondisulfide, sodium sulfate or aluminium oxide.

The novel compositions are in the form of a stable liquid concentrate, a stable working solution prepared by diluting the concentrate, a stable emulsion or a stable suspension. The composition can thus be metered easily and also has a good shelf life and does not decompose under practical conditions. The good handling properties of the composition, compared with the storage, preparation and metering in of active ingredients present in two-component systems, are advantageous.

In particular, the novel composition is in the form of a concentrate, in which case the following requirements placed on concentrates are satisfied:

- broad effectiveness (e.g. against bacteria, yeasts and fungi)
- storage stability, transportation stability and thermal stability
- relative insensitivity towards heat and light
- compatibility with packing materials
- adequate solubility in water and homogeneous distribution properties to achieve problem-free incorporation in the products to be preserved (e.g. aqueous solutions or hydrous products)
- good incorporation into anhydrous or low-water products
- vapour phase effectiveness
- adequate pH compatibility, in particular up to pH 11
- sufficiently low viscosity to enable simple metering.

The novel compositions may effectively be added to industrial products containing industrial preservatives, in particular container preservatives, fuel additives, cutting fluid preservatives, preservatives for cutting fluids which have been mixed with water, emulsions and dispersions in the coatings industry or in metalworking, household products, cosmetics and the like, so that the stability thereof and the service life of the finished products is increased compared with known systems. Increased stability of the novel compositions is particularly apparent from the lower tendency of the active ingredient to decompose, less discoloration and reduced formation of undefined decomposition products.

In addition to the customary constituents, the abovementioned industrial products thus comprise a novel composition whose components are sufficiently compatible both in the concentrate and also in the emulsion or suspension. The industrial products preferably comprise from 1 to 10% by weight, preferably from 2 to 5% by weight and in particular 2% by weight, of the novel composition.

Surprisingly, it has been found that the novel combinations of iodopropynylbutyl compounds and N- and/or O-formals, in particular the combination of iodopropynylbutyl carbamate (IPBC) and 3,3'-methylenebis(5-methyloxazolidine) (Mar 71™), have a stability which is significantly improved over the prior art, even if they are present in the form of liquid compositions, such as, for example, solutions or emulsions, in particular liquid concentrates, and are added to the abovementioned industrial products in such a form.

In addition, the effectiveness of the compositions is improved by the addition of further additives as in Patent claims 15 to 23, and, in particular, it is also possible to improve the effectiveness in the vapour phase.

Moreover, the novel compositions are adequately stable over sufficiently broad pH ranges which are relevant when the compositions are used in industrial products. Their stability is adequate in the pH range up to 12, in particular in the range up to pH 11, especially up to pH 9.

The improvements achieved in the compositions as regards stability, effectiveness and other technically relevant properties, such as pH stability and emission behavior, are illustrated by the examples below.

EXAMPLES

The following abbreviations are used in the examples below:

IPBC=iodopropynylbutyl carbamate

Mar 71™=3,3'-methylenebis(5-methyloxazolidine)

Grotan BK™=1,3,5-tris(hydroxyethyl)hexahydrotriazine

BDG=butyldiglycol

POE=phenoxyethanol

DPG=dipropylene glycol

PM=1-methoxy-2-propanol

PP=phenoxypropanol

Kathon 893™=45% strength N-octylisothiazolone solution in 1,2-propylene glycol

PE=polyethylene

PLG=propyleneglycol

Preventol D2™=benzyl alcohol hemiformal

Example 1

Compositions of IPBC and Mar 71™ with and without 1,2-propylene glycol as solvent In a test series, compositions based on (90-x)% by weight of Mar 71+x% by weight of IPBC+10% by weight of 1,2-PLG were prepared. The IPBC-containing mixtures were slightly cloudy and had to be filtered to give clear, colorless to pale yellow solutions, which were stored at a temperature of +40° C. in clear glass in order to test the stability of the compositions.

Table I shows the development, determined by means of HPLC, of the IPBC concentration of the solutions with time over a period of 3 months. Investigations were carried out on solutions having an IPBC starting content of from 0 to 10% by weight.

TABLE I

| IPBC contents: [% by wt.] | | 1 | 3 | 5 | 10 |
|---|---|---|---|---|---|
| After 1 month at + 40° C. | | 0.76 | 2.35 | 3.83 | 7.40 |
| After 2 months at + 40° C. | — | 0.62 | 1.88 | 3.04 | 5.66 |
| After 3 months at + 40° C. | 0 — | 0.52 | 1.53 | 2.49 | 4.50 |

In a second test series, compositions based on (100-x)% by weight of Mar 71™+x % by weight of IPBC without the addition of 1,2-PLG were prepared. The IPBC-containing mixtures were likewise slightly cloudy and were therefore filtered to obtain colorless to pale yellow solutions. These solutions were stored in clear glass at a temperature of +40° C. over three months. The development with time of the IPBC contents, determined by means of HPLC, is given in Table II for IPBC starting contents of from 0 to 10% by weight. The stability of the compositions in the absence of 1,2-PLG is negligibly greater, although in both cases the stability of the compositions is adequate over a sufficiently long storage period.

Furthermore, the formaldehyde emission was measured using a Dräger tube after storage for about three months at a temperature of +40° C. The formaldehyde emission was determined using Dräger tubes 67 33 081 in accordance with Dräger instructions for use no. 234–33081 (Drägerwerk AG, Germany), which involved in each case carrying out 10 strokes at 21° C. over a 50 ml wide-necked glass containing 5 g of the sample to be investigated. It was found that the formaldehyde emission increases with increasing IPBC content, as the results in the last line of Table II show. The biocidal effectiveness of the compositions in the gas phase thus also increases with increasing IPBC content in an advantageous manner.

TABLE II

| IPBC contents: [% by wt.] | 0 | 1 | 3 | 5 | 10 |
|---|---|---|---|---|---|
| After 1 month at + 40° C. | — | 0.75 | 2.17 | 3.71 | 7.08 |
| After 2 months at + 40° C. | — | 0.64 | 1.85 | 3.06 | 5.63 |
| After 3 months at + 40° C. | — | 0.58 | 1.68 | 2.69 | 4.87 |
| Formaldehyde emission [ppm] | 3 | 5 | 6–7 | 7 | 8 |

Example 2

Compositions of IPBC and various N-formals

The stability and compatibility of IPBC in compositions containing 3% by weight of IPBC, from 80 to 97% by weight of N-formals and 17% by weight of 1,2-PLG were determined as a function of the storage time after the solutions had been stored at a temperature of +40° C. in clear glass. A summary of the various percentages in the compositions is given in Table III.

The initially clear, colorless to slightly yellowish solutions became discoloured to varying degrees after storage for three months at a temperature of +40° C. Only the compositions based on IPBC and Mar 71 retained their clear, slightly yellowish appearance.

In all samples, the odor was characteristic, in some cases being pungent from the formaldehyde, and in others being amine-like. Composition F had a considerably weaker odor than composition E, which had a characteristic pungent formaldehyde odor.

TABLE III

| Composition in % by wt. | A | B | C | D | E | F | G | H |
|---|---|---|---|---|---|---|---|---|
| Grotan BK ™ | 97 | 80 | | | | | | |
| Isopropanolamine-Grotan BK with amine-excess | | | 97 | 80 | | | | |
| Mar 71 ™ | | | | | 97 | 80 | | |
| Mar 71 ™ variant with amine excess, not dewatered | | | | | | | 97 | 80 |
| IPBC | 3 | 3 | 3 | 3 | 3 | 3 | 3 | 3 |
| 1,2-PLG | — | 17 | — | 17 | — | 17 | — | 17 |
| Colour after 3 months at +40° C. | A and B: clear red-brown C and D: clear, red E and F: clear, yellowish G and H: clear, red | | | | | | | |

A summary of the development of the IPBC content, determined by means of HPLC (IPBC starting content 3% by weight) in the compositions investigated as a function of the storage period, is given in Table IV.

TABLE IV

| IPBC Contents [% by wt.] | A | B | C | D | E | F | G | H |
|---|---|---|---|---|---|---|---|---|
| After 1 month | <0.03 | 0.03 | <0.03 | <0.03 | 2.44 | 2.27 | 0.73 | 0.94 |
| After 2 months | <0.03 | | | | 2.04 | 1.78 | 0.53 | 0.72 |
| After 3,5 months | | | | | 1.61 | 1.34 | <0.01 | 0.04 |

It is found that IPBC is compatible with different N-formals to varying degrees. Incompatibility is apparent in particular from a relatively high degree of discoloration following storage and a relatively high degree of IPBC degradation. Thus, for example, the low-odor Grotan BK TM is incompatible with IPBC. In contrast, preparations based on IPBC and Mar 71 TM with or without 1,2-PLG are significantly more stable and, after storage for three months at +40° C. display on IPBC degradation of only about 50%. The formaldehyde emission increases with increasing IPBC content. The addition of 1,2-PLG to compositions which comprise Mar 71 and IPBC is therefore unfavourable for the stability, but has an advantageous effect on the odor of the compositions.

Example 3

Stability of IPBC and Mar 71 in various solvents

The dependence of the IPBC stability in compositions of IPBC and Mar 71™ on various solvents used was tested by storing the compositions in clear glass at a temperature of +40° C. Investigations were carried out on preparations containing 1 or 3% by weight of IPBC combined with 89 or 87% by weight of Mar 71™ respectively and in each case 10% by weight of a solvent. The results are given in Tables V and VI.

TABLE V

| | A | C | E | G | I | K |
|---|---|---|---|---|---|---|
| Composition [% by wt.] | | | | | | |
| Mar 71 | 89 | 89 | 89 | 89 | 89 | 89 |
| IPBC | 1 | 1 | 1 | 1 | 1 | 1 |
| 1,2-PLG | 10 | — | — | — | — | — |
| DPG | — | 10 | — | — | — | — |
| BDG | — | — | 10 | — | — | — |
| PM | — | — | — | 10 | — | — |
| POE | — | — | — | — | 10 | — |
| PP | — | — | — | — | — | 10 |
| IPBC Content [% by wt.] | | | | | | |
| After 1 month at + 40° C. | 0.74 | 0.75 | 0.74 | 0.77 | 0.76 | 0.75 |
| After 2 months at + 40° C. | 0.63 | 0.66 | 0.61 | 0.62 | 0.57 | 0.68 |
| After 3 months at + 40° C. | 0.56 | 0.57 | 0.54 | 0.60 | 0.60 | 0.60 |
| Formaldehyde emission* (in ppm) | 4 | 5 | 3 | 2 | 5 | 5 |

*= measured as described in Example 1 using Dräger tubes (10 strokes) at 21° C. after storage for about 3 months at + 40° C. on 5 g in each case in a 50 ml wide-necked glass.

TABLE VI

| | B | D | F | H | J | L |
|---|---|---|---|---|---|---|
| Composition [% by wt.] | | | | | | |
| Mar 71 | 87 | 87 | 87 | 87 | 87 | 87 |
| IPBC | 3 | 3 | 3 | 3 | 3 | 3 |
| 1,2-PLG | 10 | — | — | — | — | — |
| DPG | — | 10 | — | — | — | — |
| BDG | — | — | 10 | — | — | — |
| PM | — | — | — | 10 | — | — |
| POE | — | — | — | — | 10 | — |
| PP | — | — | — | — | — | 10 |
| IPBC Content [% by wt.] | | | | | | |
| After 1 month at + 40° C. | 2.12 | 2.20 | 2.15 | 2.21 | 2.21 | 2.17 |
| After 2 months at + 40° C. | 1.72 | 1.75 | 1.89 | 1.90 | 1.84 | 1.77 |
| After 3 months at + 40° C. | 1.50 | 1.57 | 1.47 | 1.57 | 1.52 | 1.57 |
| Formaldehyde emission* (in ppm) | 5 | 6 | 6–7 | 4 | 6 | 8 |

*= measured as described in Example 1 using Dräger tubes (10 strokes) at 21° C. after storage for about 3 months at + 40° C. on 5 g in each case in a 50 ml wide-necked glass.

It has been found that the IPBC content of the preparations, determined by means of HPLC, continually decreases throughout the storage time. The effect of the solvent on the IPBC stability in the presence of Mar 71 is not very great. All investigated compositions showed an IPBC degradation of about 50% after storage for 3 months in clear glass at +40° C. In both test series, the greatest IPBC degradation was in butyldiglycol (BDG). In contrast, relatively suitable solvents for the novel compositions are: dipropylene glycol (DPG), 1-methoxy-2-propanol (PM), phenoxypropanols (PP) and phenoxyethanol.

There were clear differences in the formaldehyde emission determination. As Tables V and VI show, a composition containing 1-methoxy-2-propanol performs particularly well. For example, compared with all the other solvents, the formaldehyde emission was reduced by up to about 50% after three months through the addition of 1-methoxy-2-propanol.

Example 4

Stability of IPBC with various formals

The stability of various IPBC compositions was tested in clear glass at temperatures of +25° C. and +40° C. Investigations were carried out with preparations containing 10% by weight of IPBC and 90% of formals. The results are given in Tables VII and VIII.

TABLE VII

| Composition [% by wt.] | M | N | O |
|---|---|---|---|
| IPBC | 10 | 10 | 10 |
| Mar 71 ™ | 90 | — | — |
| Preventol D2 ™ | — | 90 | — |
| PLG hemiformal | — | — | 90 |

TABLE VIII

| | IPBC loss of weight [% wt.] | | | | | | | |
|---|---|---|---|---|---|---|---|---|
| | after 5 weeks | | after 5.5 weeks | | after 6.5 weeks | | after 3 months | |
| composition | at 25° C. | at 40° C. | at 25° C. | at 40° C. | at 25° C. | at 40° C. | at 25° C. | at 40° C. |
| M | — | — | — | — | 1.49 | 19.13 | — | — |
| N | 6.4 | 31.1 | — | — | — | — | — | — |
| O | — | — | 26.25 | 64.90 | — | — | 58.33 | 69.79 |

Example 5

Stability of IPBC compositions containing further additives

Various additives were added to the compositions M and N and the stability of the resulting preparations were investigated as hereabove mentioned in example 7; the results are given in tables IX and X.

TABLE IX

| Composition [% by wt.] | M1 | M2 | M3 | M4 | N1 |
|---|---|---|---|---|---|
| IPBC | 10 | 10 | 10 | 10 | 10 |
| Mar 71 ™ | 88 | 88 | 88 | 88 | — |
| Preventol D2 ™ | — | — | — | — | 88 |
| Triethanolamine | 2 | — | — | — | 2 |
| Pyriondisulfide ™ | — | 2 | — | — | — |
| Anhydrous sodium sulfate | — | — | 2 | — | — |
| Aluminium oxide 90 ™ (Merck) | — | — | — | 2 | — |

TABLE X

| | IPBC loss of weight [% wt.] | | | |
|---|---|---|---|---|
| | after 5 weeks | | after 6.5 weeks | |
| Composition | at 25° C. | at 40° C. | at 25° C. | at 40° C. |
| M | — | — | 1.49 | 19.13 |
| M1 | — | — | 3.93 | 22.85 |
| M2 | — | — | 0.0 | 15.84 |
| M3 | — | — | 3.83 | 22.0 |
| M4 | — | — | 1.93 | 13.79 |
| N | 6.4 | 31.1 | — | — |
| N1 | 2.5 | 15.8 | — | — |

Example 6

Odor modification of Mar 71™ by the addition of O-formals

Compositions containing Mar 71™ with and without 1, 2, 5 and 10% by weight of 1,2-propylene glycol hemiformal were stored at room temperature in clear glass. The preparations proved to be sufficiently stable. However, over time a very slightly cloudy sediment formed in the mixtures. The addition of 1,2-propylene glycol hemiformal resulted in a clear positive odor modification of Mar 71™.

Example 7

Compositions based on Mar 71™ containing other biocides

The stability of compositions which, in addition to 83-x % by weight of Mar 71™, comprise as further biocide 17% by weight of N-octalisothiazolone (i.e. a 45% strength N-octylisothiazolone solution in 1,2-PLG=Kathon 893), was tested by storage in clear glass at room temperature. As well as Mar 71™ and Kathon 893™, the formulations in some instances comprised 1, 2, 5 and 10% by weight of 1,2-propylene glycol hemiformal. The preparations were found to be stable. In contrast to the compositions without Kathon 893™, no cloudy sediment formed here. The addition of 1,2-propylene glycol hemiformal resulted in a clear positive odor modification of Mar 71™.

Example 8

Stability of compositions containing IPBC and various N-formals

The stability of a composition containing 3% by weight of IPBC, 80% by weight of Mar 71™ and 17% by weight of 1,2-PLG was determined by storage in polyethylene at room temperature and at +40° C. The composition stored at room temperature was unchanged, i.e. clear and colorless, after 14 months. The IPBC contents of the investigated compositions, determined by means of HPLC, are given in Table VII. The test proves that the combination of Mar 71™+IPBC+1,2-PLG is sufficiently stable at various temperatures.

TABLE XI

|  | RT | +40° C. |
|---|---|---|
| IPBC content [% by wt] after 1 month | 2.63 | 2.32 |
| IPBC content [% by wt] after 3 months | 2.59 | 1.28 |
| IPBC content [% by wt] after 8 months | 2.22 | 0.59 |

As well as Mar 71™, the compatibility of IPBC with 3,3'-methylenebis(tetrahydro-2H-1,3-oxazine) as a further N-formal was investigated. In addition to IPBC (3% by weight) and the corresponding N-formal (80% by weight), both compositions also additionally comprise 17% by weight of 1,2-propylene glycol. The IPBC content was determined after storage at room temperature after 1, 3 and 11 months. It has been found that a combination of IPBC and 3,3'-methylenebis(tetrahydro-2H-1,3-oxazine) is also sufficiently stable. As Table VIII shows, the IPBC content was still 2.09% by weight after storage for 11 months at room temperature, if 3,3'-methylenebis(tetrahydro-2H-1,3-oxazine) was used as N-formal.

TABLE XII

| Composition [% by wt.] | C1 | D | C2 |
|---|---|---|---|
| Mar 71 ™ | 80 | — | 80 |
| 3,3'-Methylenebis(tetrahydro-2H-1,3-oxazine | — | 80 | — |
| IPBC | 3 | 3 | 3 |
| 1,2-PLG | 17 | 17 | 17 |
| IPBC content zero value | — | — | 2.92 |
| IPBC content after 1 month at RT | — | — | 2.88 |
| IPBC content after 3 months at RT | 2.29 | 2.81 | — |
| IPBC content after 11 months at RT | — | 2.09 | — |

Example 9

Formaldehyde emission of N-formals

As well as characterizing their compatibility and stability with IPBC, the N-formals Mar 71™ and 3,3'-methylenebis(tetrahydro-2H-1,3-oxazine) were tested with regard to their formaldehyde emission behavior and odor.

For this purpose, 1 g of each of the N-formals was left to stand overnight in a 400 ml beaker covered with para-film. On the following day, the formaldehyde content was then measured using Dräger tubes (10 strokes) as described in Example 1.

The formaldehyde content was 15 ppm (2 strokes 3 ppm) in 3,3'-methylenebis(tetrahydro-2H-1,3-oxazine) and 25 ppm (2 strokes 5 ppm) in Mar 71™. Preparations of 80% by weight of each N-formal and 20% by weight of 1,2-propylene glycol display a clearly different behavior. For example, the addition of 1,2-PLG to 3,3'-methylenebis (tetrahydro-2H-1,3-oxazine) leads to a reduction in the formaldehyde content to form 1.5 to 2.5 ppm (20 strokes) and the addition to Mar 71™ to a reduction to 10 ppm (5 strokes 5 ppm), the formaldehyde content being determined as described above for pure N-formals. The experiment shows that the addition of propylene glycol significantly reduces the formaldehyde emission of the N-formals according to the invention.

We claim:
1. Composition having broad effectiveness against bacteria and fungi, which comprises:
   (a) an iodopropynylbutyl compound selected from the group consisting of iodopropynylbutyl esters, ethers, acetals, carbamates and carbonates, and
   (b) a N-formal selected from the group consisting of 3,3'-methylene bis(5-methyloxazolidine), 3,3'-methylene bis(tetrahydro-2H-1,3-oxazine) and 1-aza-5-ethyl-3,7-dioxabicyclo(3,3,0)octane, or a combination thereof.
2. Composition according to claim 1, wherein the iodopropynylbutyl compound is iodopropynylbutyl carbamate (IPBC).
3. Composition according to claim 1, wherein the N-formal is 3,3'-methylene bis(5-methyloxazolidine).
4. Composition according to claim 1, which further comprises one or more O-formal formed by the reaction of a monovalent or polyvalent, amino-substituted C1–C10 -alkyl, aryl, aralkyl alcohol or of a glycol or glycolether and a formaldehyde-supplying compound.
5. Composition according to claim 4, wherein the O-formals are selected from polyoxymethylene glycols, polyoxymethylene diacetates and polyoxymethylene dimethyl ethers.
6. Composition according to claim 4, wherein the O-formal is formed by the reaction of 1,2-propylene glycol, dipropylene glycol, ethylene glycol, butyl glycol, butyl diglycol or benzyl alcohol, and a formaldehyde-supplying compound.
7. Composition according to claim 1, wherein the iodopropynylbutyl compound is iodopropynylbutyl carbamate and a formaldehyde donor compound is 3,3'-methylenebis(5-methyloxazolidine).
8. Composition according to claim 1, wherein the composition comprises the following components:
   a) from 0.1 to 20% by weight of said iodopropynylbutyl compound; and
   b) from 99.9% to 80% by weight of said N-formal.
9. Composition according to claim 8, wherein the composition comprises the following components:
   a) from 4 to 6% by weight of said iodopropynylbutyl carbamate; and
   b) from 96 to 94% by weight of said 3,3'-methylenebis (5-methyloxazolidine).
10. Composition according to claim 1, wherein the composition comprises the following components:
   a) from 0.1 to 20% by weight of said iodopropynylbutyl compound; and
   b) from 99.9 to 80% by weight, of a mixture of said N- and O-formals the weight ratio of N- to O-formals being from 10:1 to 1:10.
11. Composition according to claim 10, wherein the composition comprises the following components:
   a) from 4 to 6% by weight of said iodopropynylbutyl carbamate; and
   b) from 96 to 94% by weight of a mixture of said 3,3'-methylenebis(5-methyloxazolidine) and 1,2-propylene glycol hemiformal.
12. Composition according to claim 1, wherein the composition is in stable liquid, viscous liquid or paste form.
13. Composition according to claim 1, wherein the composition further comprises at least one of emission-reducing additives, viscosity-modifying additives, wetting agents, stabilizers and solvents.
14. Composition according to claim 13, wherein the solvents reduce the emission of formaldehyde or formaldehyde-containing substances.

15. Composition according to claim 14, wherein the solvent is selected from 1,2-propylene glycol, 1-methoxy-2-propanol, phenoxypropanol and phenoxyethanol.

16. Composition according to claim 13, wherein the composition comprises the following components:
 a) from 0.1 to 20% by weight of said iodopropynylbutyl compound; and
 b) from 99.9 to 80% by weight of a mixture of N-formals and solvents or of a mixture of a combination of N- and O-formals and solvents, the weight ratio of formal to solvent being from 50:1 to 1:10.

17. Composition according to claim 16, wherein the composition comprises the following components:
 a) from 4 to 6% by weight of an iodopropynylbutyl compound; and
 b) from 96 to 94% by weight of the mixture of N-formals and solvents or the mixture of the combination of N- and O-formals and solvents, the ratio of formals to solvents being from 50:1 to 1:10.

18. Composition according to claim 1, wherein the composition additionally comprises biocidal ingredients selected from the group consisting of isothiazolone, N-octylisothiazolone, and 2-mercaptopyridine-N-oxide.

19. Composition according to claim 13, which comprises between 1% and 10% by weight of said IPBC, between 85% and 98.5% by weight of a stabilizer selected from triethanolamine, pyriondisulfide, sodium sulfate or aluminum oxide.

20. Composition according to claim 1, wherein the composition is in the form of a stable liquid concentrate, a stable working solution prepared by diluting the concentrate, a stable suspension or a stable emulsion.

21. Method of increasing the stability and service life of industrial products containing industrial preservatives selected from the group consisting of container preservatives, fuel additives, cutting fluid preservatives, preservatives which have been mixed with water, emulsions and dispersions in the coatings industry or in metal working, household products, and cosmetics, which comprises adding a biocidally effective amount of the composition of claim 1 to the industrial product as an active agent.

22. Industrial product which comprises as an active agent, a biocidally effective amount of the composition of claim 1, said industrial product comprising industrial preservatives selected from the group consisting of container preservatives, fuel additives, cutting fluid preservatives, preservatives which have been mixed with water, emulsions and dispersions in the coatings industry or in metal working, household products, and cosmetics.

23. The industrial product according to claim 22, wherein the composition is present from 1 to 10% by weight.

24. The industrial product according to claim 23, wherein the composition is present from 2 to 5% by weight.

* * * * *